(12) United States Patent
Edie et al.

(10) Patent No.: US 7,142,629 B2
(45) Date of Patent: Nov. 28, 2006

(54) STATIONARY COMPUTED TOMOGRAPHY SYSTEM AND METHOD

(75) Inventors: Peter Michael Edie, Albany, NY (US); Bruno Kristiaan Bernard De Man, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 80 days.

(21) Appl. No.: 10/814,537

(22) Filed: Mar. 31, 2004

(65) Prior Publication Data

US 2005/0226363 A1  Oct. 13, 2005

(51) Int. Cl.
*G01N 23/00* (2006.01)
(52) U.S. Cl. .............................. 378/9; 378/4
(58) Field of Classification Search ............ 378/9, 378/10, 11, 21, 22, 4, 12, 17, 19, 62, 122, 378/136
See application file for complete search history.

(56) References Cited

U.S. PATENT DOCUMENTS

| | | | | |
|---|---|---|---|---|
| 4,126,786 A | * | 11/1978 | LeMay et al. | 378/7 |
| 4,153,842 A | * | 5/1979 | Rohmfeld | 378/9 |
| 4,206,362 A | * | 6/1980 | Bagby | 378/9 |
| 4,347,624 A | * | 8/1982 | Tschunt | 378/10 |
| 4,592,080 A | * | 5/1986 | Rauch et al. | 378/19 |
| 4,958,365 A | * | 9/1990 | Sohval et al. | 378/122 |
| 5,195,112 A | * | 3/1993 | Vincent et al. | 378/10 |

OTHER PUBLICATIONS

Merriam-Webster's Collegiate Dictionary, 10th Ed., 2001, pp. 797, 1252.*

* cited by examiner

*Primary Examiner*—Edward J. Glick
*Assistant Examiner*—Hoon Song
(74) *Attorney, Agent, or Firm*—Fletcher Yoder (57) ABSTRACT

A radiological imaging system includes one or more radiation sources substantially surrounding a desired portion of an imaging volume and configured to emanate a radiation beam from a plurality of individual source positions around the imaging volume, and one or more detectors configured to receive the transmitted radiation beam. At least one of the radiation source and the detector are displaceable to allow an unimpeded path for the radiation beam and to receive the transmitted radiation beam more completely.

27 Claims, 6 Drawing Sheets

STATIONARY COMPUTED TOMOGRAPHY SYSTEM AND METHOD

BACKGROUND

The present invention relates generally to the field of computed tomography (CT) imaging systems and specifically to source and detector configurations for stationary CT systems to facilitate measurement of more complete data for image reconstruction.

Computed tomography is a technique which creates two-dimensional cross-sectional images or three-dimensional volumetric images from three-dimensional structures. The CT imaging system primarily includes a CT gantry and a patient table or a couch. The gantry is a moveable frame that contains an X-ray source, which is typically an X-ray tube including collimators and filters on one side, and detectors with an associated data acquisition system (DAS) on an opposite side. The gantry typically also includes rotational components requiring slip-ring systems and all associated electronics, such as gantry angulation motors and positioning laser lights.

In known, so called "third generation" CT systems (source and detector configured in a fixed arrangement that itself either rotates or is combined with a device that rotates the object of interest), the X-ray source and the detector array are rotated with a gantry within the imaging plane and around the object to be imaged, so that the angle at which the X-ray beam intersects the object constantly changes. As mentioned, X-ray sources typically include X-ray tubes, which emit the X-ray beam from a focal spot. An X-ray detector may include a crystal or ionizing gas that, when struck by an X-ray photon, produces light or electrical energy. The three exemplary types of detectors utilized in CT systems are scintillation, gas ionization, or direct conversion detectors. The CT systems may typically include post-patient collimators for reducing scattered radiation at the detector. These systems have limitations regarding rotational speeds, mechanical balancing of the systems, power and thermal requirements, which become increasingly complex due to the rotational components.

Other types of CT architectures, which include stationary CT designs, offer high scanning speeds, and incorporate mechanisms for directing a high-intensity electron beams onto stationary X-ray targets to produce X-rays (electron-beam CT systems). There are, however, challenges with respect to acquiring more complete image data in these stationary CT configurations. In stationary CT systems of the type described above, both the X-ray source and the detector are stationary, circling either the entire gantry or a substantial part of the gantry.

An alternative stationary CT system design includes a distributed X-ray source that either encircles the entire gantry or is of sufficient extent to facilitate imaging scenarios. The X-ray source is typically comprised of several discrete electron emitters. Since both the X-ray source and detector are stationary in stationary CT configurations, they need to be designed to facilitate appropriate scanning protocols. In a preferred axial scanning configuration, the distributed X-ray sources at both longitudinal extents of a centered detector may be slightly offset (vertically and/or radially) relative to the area detector array. As a result, a volume in the center of the field of view of the imaging system is not subjected to X-rays, prohibiting reconstruction in this volume. In a preferred helical scanning configuration, a distributed X-ray source is placed between two area detectors that circle the entire gantry. The X-rays are emitted through a gap between the two detector arrays to administer X-ray flux to the imaging volume. Because the X-ray source is also distributed around the entire gantry, the gap encircles the entire gantry, which prohibits measurement of CT projection data and artifact-free image reconstruction within the corresponding volume.

It is therefore desirable to provide improved source and detector configurations for stationary CT systems to facilitate measurement of more complete data for image reconstruction.

BRIEF DESCRIPTION

Briefly in accordance with aspects of present technique, an imaging system includes a radiation source at least substantially surrounding a desired portion of an imaging volume and configured to emanate a radiation beam from a plurality of individual positions around the imaging volume, and a detector configured to receive the radiation beam upon attenuation. At least one of the radiation source and the detector is displaceable to allow an unimpeded path for the X-ray source to provide a radiation beam which illuminates a volume of interest and a detector configuration to receive the radiation beam.

In accordance with another aspect, a method for scanning a desired portion of an imaging volume is provided. The method includes triggering a radiation source which emanates a radiation beam, displacing a first detector positioned generally adjacent to the radiation source enabling an unimpeded path for the radiation beam to illuminate a volume of interest, and displacing a second detector positioned generally opposite to the radiation source to measure the transmitted radiation beam.

DRAWINGS

These and other features, aspects, and advantages of the present invention will become better understood when the following detailed description is read with reference to the accompanying drawings in which like numerical labels represent like parts throughout the drawings, wherein.

DETAILED DESCRIPTION

Figure 1:
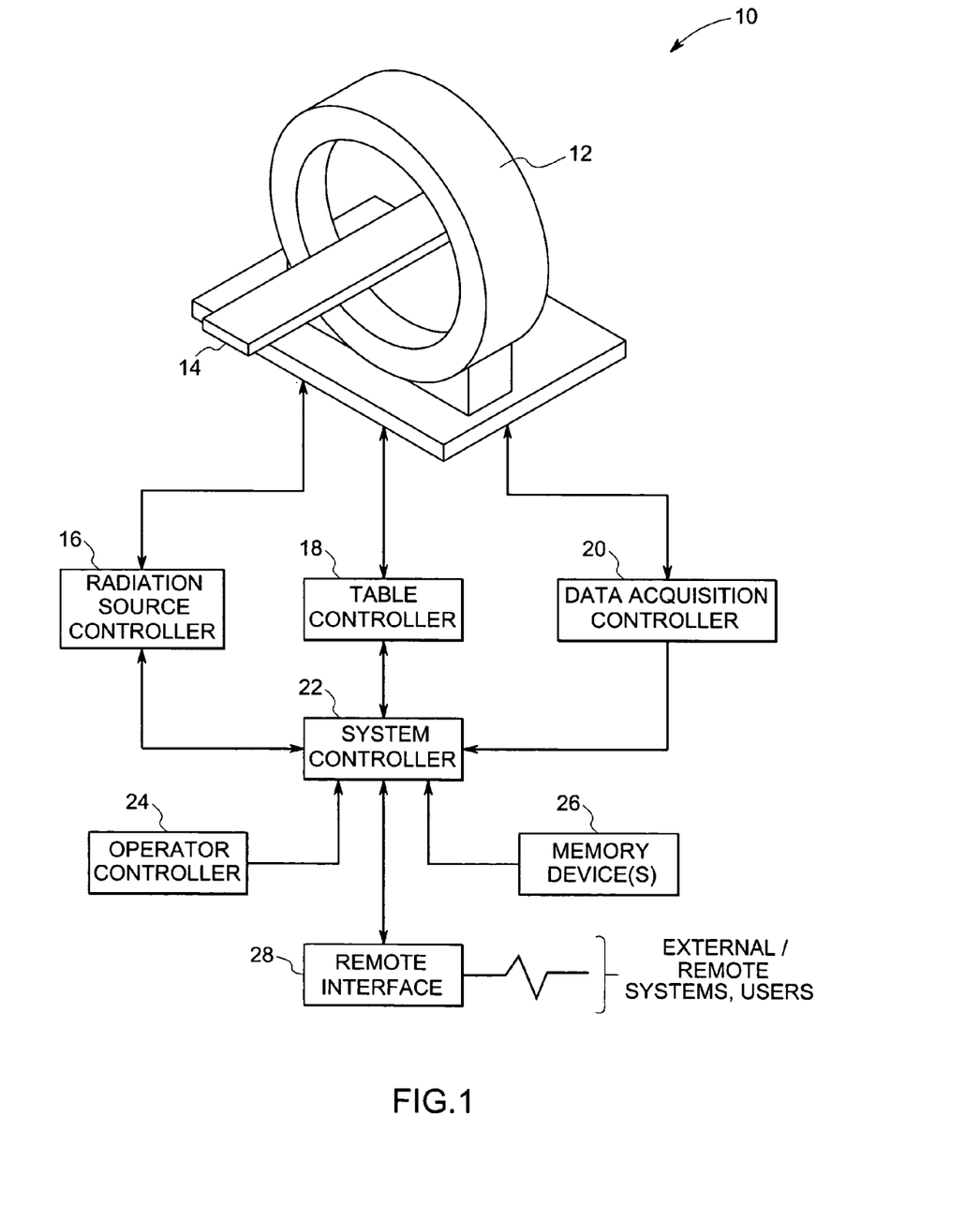
FIG. 1 is a diagrammatical representation of an exemplary stationary CT system in accordance with aspects of the present technique.

Referring to now FIG. 1, a computed tomography (CT) system is illustrated and designated generally by reference numeral 10. The CT system 10 comprises a scanner 12 formed of a support structure and internally containing one or more stationary and distributed sources of X-ray radiation (not shown in FIG. 1) and one or more stationary digital detectors (not shown in FIG. 1), as described in greater detail below. The scanner is configured to receive a table 14 or other support for a patient, or, more generally, a subject to be scanned. The table can be moved through an aperture in the scanner to appropriately position the subject in an imaging volume scanned during imaging sequences.

The system further includes a radiation source controller 16, a table controller 18 and a data acquisition controller 20, which may all function under the direction of a system controller 22. The radiation source controller 16 regulates timing for discharges of X-ray radiation which is directed from points around the scanner 12 toward a detector segment on an opposite side thereof, as discussed below. In the present stationary CT arrangements, the radiation source controller 16 may trigger one or more emitters in a distributed X-ray source at each instant in time for facilitating multiple acquisitions of transmitted X-ray intensity data. In certain arrangements, for example, the X-ray radiation source controller 16 may trigger emission of radiation in sequences so as to collect adjacent or non-adjacent acquisitions of transmitted X-ray intensity around the scanner. Many such measurements may be collected in an examination sequence, and data acquisition controller 20, coupled to detector elements as described below receives signals from the detector elements and processes the signals for storage and later image reconstruction. In other configurations, the signals may be processed in real-time to generate reconstructions of patient within the imaging volume of the gantry. Table controller 18, then, serves to appropriately position the table and subject in a plane in which the radiation is emitted, or, in the present context, generally within a volume to be imaged. The table may be displaced between imaging sequences or during certain imaging sequences, depending upon the imaging protocol employed.

System controller 22 generally regulates the operation of the radiation source controller 16, the table controller 18 and the data acquisition controller 20. The system controller 22 may thus cause radiation source controller 16 to trigger emission of X-ray radiation, as well as to coordinate such emissions during imaging sequences defined by the system controller. The system controller may also regulate movement of the table in coordination with such emission so as to measure transmitted X-ray intensity data from volumes of particular interest, or in various modes of imaging, such as for axial or helical modes. The system controller 22 also receives data acquired by data acquisition controller 20 and coordinates storage and processing of the data. Although shown as separate entities in FIG. 1, one or more of the radiation source controller 16, the table controller 18, and the data acquisition controller 20 may be included in the system controller 22.

It should be borne in mind that the controllers, and indeed various circuitry described herein, may be defined by hardware circuitry, firmware or software. The particular protocols for imaging sequences, for example, will generally be defined by code executed by the system controllers. Moreover, initial processing, conditioning, filtering, and other operations performed on the transmitted X-ray intensity data acquired by the scanner may be performed in one or more of the components depicted in FIG. 1. For example, as described below, detector elements may produce analog signals representative of depletion of a charge in photodiodes positioned at locations corresponding to elements of the acquisition detector. Such analog signals are converted to digital signals by electronics within the scanner, and are transmitted to data acquisition controller 20. Partial processing may occur at this point, and the signals are ultimately transmitted to the system controller for further filtering and processing.

System controller 22 is also coupled to an operator interface 24 and to one or more memory devices 26. The operator interface may be integral with the system controller, and will generally include an operator workstation and/or keyboard for initiating imaging sequences, controlling such sequences, and manipulating data acquired during imaging sequences. The memory devices 26 may be local to the imaging system, or may be partially or completely remote from the system. Thus, memory devices 26 may include local, magnetic or optical memory, or local or remote repositories for imaged data for reconstruction. Moreover, the memory devices may be configured to receive raw, partially processed or fully processed data for reconstruction.

System controller 22 or operator interface 24, or any remote systems and workstations, may include software for image processing and reconstruction. As will be appreciated by those skilled in the art, such processing of CT data may be performed by a number of mathematical algorithms and techniques. For example, conventional filtered back-projection techniques may be used to process and reconstruct data acquired by the imaging system. Other techniques, and techniques used in conjunction with filtered back-projection may also be employed. A remote interface 28 may be included in the system for transmitting data from the imaging system to such remote processing stations, memory devices, or image display devices.

Figure 2:
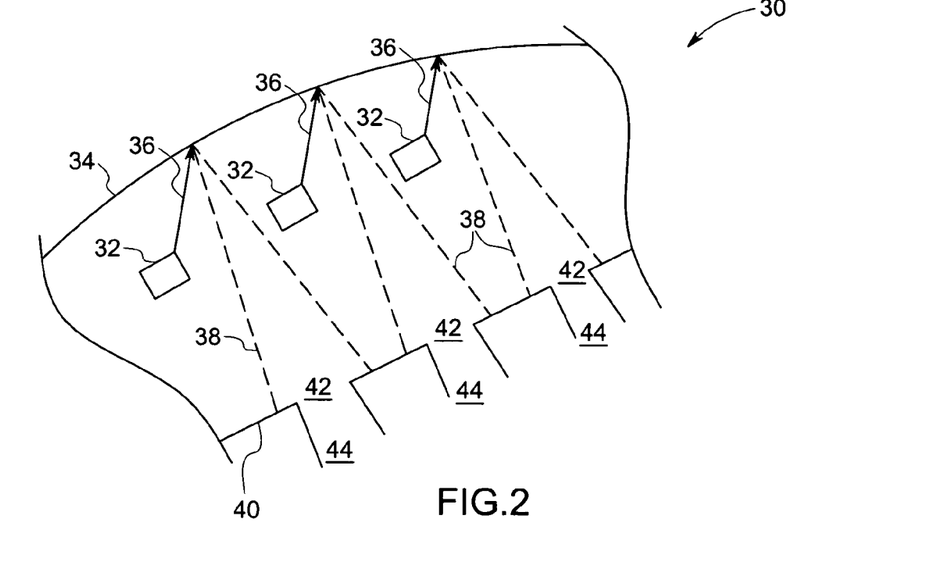
FIG. 2 is a diagrammatical representation of an exemplary distributed source for use with a system of the type illustrated in FIG. 1.

The scanner 12 of stationary CT system 10 preferably includes one or more distributed X-ray sources as well as one or more digital detectors for receiving radiation and processing corresponding signals to produce image data. FIG. 2 illustrates a portion of an exemplary distributed X-ray source of the type that may be employed in the stationary CT system. As shown in FIG. 2, in an exemplary implementation, the distributed X-ray source 30 may include a series of electron beam emitters 32 that are coupled to radiation source controller 16 shown in FIG. 1, and are triggered by the source controller during operation of the scanner. The electron beam emitters 32 are positioned proximal to a target 34. Upon triggering by the radiation source controller 16, the electron beam emitters 32 may emit electron beams 36 toward target 34. The target 34, which may, for example, be a tungsten rail or element, emits X-ray radiation, as indicated at reference numeral 38, upon impact of the electron beams thereon. The X-ray source may be operated in either reflection or transmission mode. In reflection mode as shown in FIG. 2, X-rays are meant to be produced primarily on the same side of the target as where the electrons impact. In transmission mode, X-rays are meant to be produced at the opposite side of the target from where the electron beam impacts the target. The X-ray beams 38 are directed, then, toward an optional collimator 40, which is generally opaque to the X-ray radiation, but which includes apertures 42. The apertures 42 may be fixed in dimension, or may be adjustable. Apertures 42 permit a portion of the X-ray beams to penetrate through the collimator to form collimated beams 44 that will be directed to the imaging volume of the scanner, through the subject of interest, and that will impact detector elements on an opposite side of the scanner.

A number of alternative configurations for emitters or distributed sources may, of course, be envisaged. Moreover, the individual X-ray sources in the distributed source may emit various types and shapes of X-ray beams. These may include, for example, fan-shaped beams, cone-shaped beams, and specially filtered beams to facilitate both the imaging scenario and dose administered to the patient. Similarly, the various components comprising the distributed X-ray source may also vary. In one embodiment, for example, a cold cathode emitter is envisaged which will be housed in a vacuum housing. A stationary anode is then disposed in the housing and spaced apart from the emitter. This type of arrangement generally corresponds to the diagrammatical illustration of FIG. 2. Other materials, configurations, and principals of operations may, of course, be employed for the distributed source. For example, one emission device may be configured to transmit an electron beam to multiple locations on the target in order to produce multiple X-ray radiation beams. The emission devices may be one of many available electron emission devices, for example, thermionic emitters, cold-cathode emitters, carbon-based emitters, photo emitters, ferroelectric emitters, laser diodes, monolithic semiconductors, etc.

As discussed in greater detail below, the present stationary CT techniques are based upon use of a plurality of distributed and addressable electron emission sources for generation of X-ray radiation, denoted distributed sources of radiation. Moreover, the distributed sources of radiation may be associated in single unitary enclosures or vacuum enclosure or in a plurality of vacuum enclosures designed to operate in cooperation. The individual sources are addressable independently and individually so that radiation can be triggered from each of the sources at points in time during the imaging sequence as defined by the imaging protocol. In other configurations, the sources are addressable in logical groups, for example pairs or triplets of emitters may be wired together. Where desired, more than one such source may be triggered concurrently at any instant in time, or the sources may be triggered in specific sequences to mimic rotation of a gantry, or in any desired sequence around the imaging volume or plane.

Figure 3:
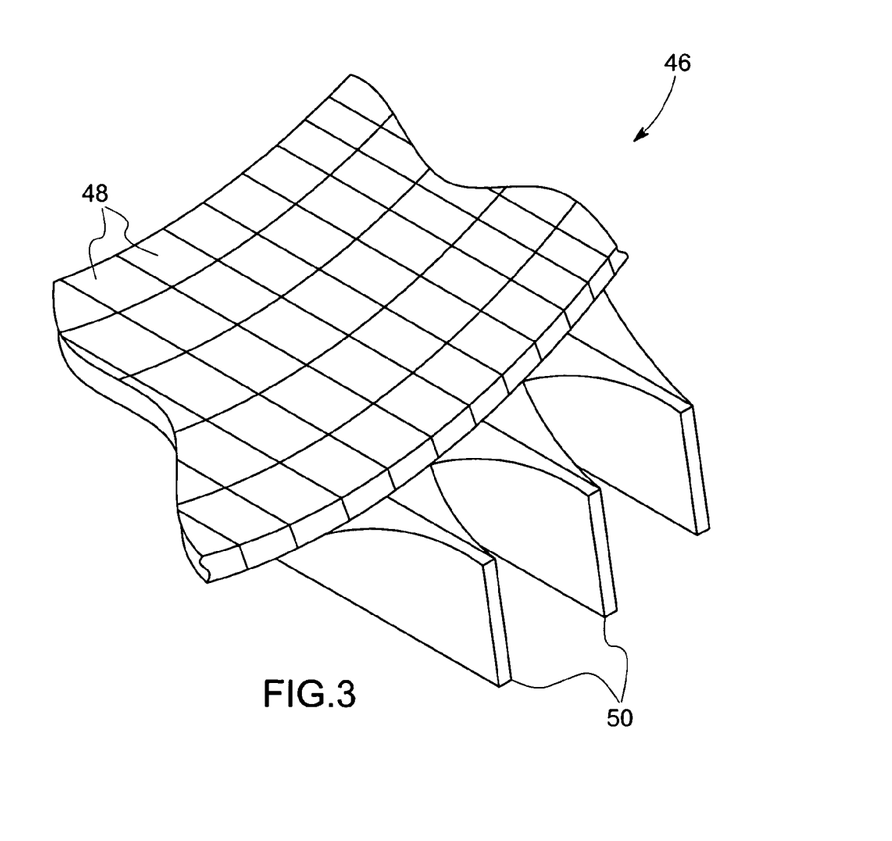
FIG. 3 is a diagrammatical representation of a portion of a detector for use with the system of FIG. 1.

A plurality of detector elements form one or more detectors which receive the radiation emitted by the distributed sources of radiation. FIG. 3 illustrates a portion of a detector, which may be employed for the present purposes. Each detector may be composed of detector elements with varying resolution to satisfy a particular imaging application. The detector arrangement may be generally similar to detectors used in conventional rotational CT systems, but is extended around a greater portion or the entire circumference of the scanner. In general, the detector 46 includes a series of detector elements 48 and associated signal processing circuitry 50. Each detector element may be a scintillation-type device and include a photodiode and associated thin film transistors. X-ray radiation impacting the detectors is converted to lower energy photons by a scintillator and these photons impact the photodiodes. A charge maintained across the photodiodes is thus depleted, and the transistors may be controlled to recharge the photodiodes and thus measure the depletion of the charge. By sequentially measuring the charge depletion in the various photodiodes, each of which corresponds to a detector element or pixel in the collected data for each acquisition, data is collected that encodes transmitted radiation at each of the pixel locations. This data is processed by the signal processing circuitry 50, which will generally convert the analog signals to digital values, possibly perform required filtering, and transmit the acquired data to processing circuitry of the imaging system as described above. Although the detector has been described in terms of a scintillator-based energy-integrating device, other detector types such as gas-ionization, direct-conversion, photon-counting, or energy-discriminating detectors are equally suitable.

A large number of detector elements 48 may be associated in the detector so as to define many rows and columns of individual detector elements. As described below, the detector configurations of the present technique position detector elements across from independently addressable distributed X-ray sources so as to permit a large number of view acquisitions to be collected for image reconstruction.

As will be appreciated by those skilled in the art, reconstruction techniques in CT systems vary in their use of acquired data, and in their techniques and assumptions for image reconstruction. It will be appreciated by those skilled in the art that a number of geometries are available for high-speed and efficient operation of a stationary CT system, which provide data for accurate image reconstruction.

Many of the presently contemplated geometries include sources and/or detectors that encircle the entire gantry. However, certain of these concepts can be reduced to less expensive and equally or generally satisfactorily-performing configurations by eliminating a portion of the complete ring in these structures. Depending upon the image reconstruction technique employed, for example, detectors extending around 180 degrees plus the fan angle of the emitted X-ray beams may be sufficient for excellent data collection and image construction.

For mechanical reasons, there are gaps between sources and detectors at interfaces. Such gaps may be accounted for by additional measurements from sources and/or detectors, according to aspects of present technique, which enable measurement of the missing data. Moreover, the configurations described below are contemplated for both axial, helical, or other appropriate scan modes. Depending upon the particular application, however, certain of the configurations may be more suited to one or more of these modes, such as to the axial mode for medical applications and helical modes for applications such as baggage scanning. Also the sources and detectors described in the configurations below may have different diameters, sizes, extents, and so forth. Moreover, the sources and detectors may be composed of linear sections, planar sections, or other spatially distributed sections, which approximate the configurations discussed below.

In the present technique as shown in FIGS. 4-10, a radiation imaging system includes at least one radiation source substantially surrounding a desired portion of an imaging volume and is configured to emanate a radiation beam from a number of different individual positions around the imaging volume. At least one detector is configured to receive the X-ray radiation upon being attenuated by the patient. In these configurations at least one detector section is displaceable to allow an unimpeded path for the radiation beam to illuminate a desired portion of the imaging volume and for one or more other detector sections to receive the radiation beam more completely. In certain configurations, at least one of the distributed sources is configured to move to illuminate the desired portion of the imaging volume for measurement of more mathematically complete projection data. As it would be appreciated by those skilled in the art and as explained hereinabove with reference to the description of X-ray sources for stationary CT applications, in a specific stationary CT system, a plurality of X-ray sources are arranged relative to a volume to be imaged and each X-ray source is configured to emanate an X-ray beam. In specific configurations a plurality of detectors (or detector elements) are arranged generally across from respective X-ray sources, each detector configured to be displaced to allow an unimpeded path for the radiation beam to illuminate the desired portion of the imaging volume and to receive the radiation beam for measurement of more mathematically complete projection data. In general, FIGS. 4-10 include non-limiting examples of embodiments of present technique to be implemented in the above described source-detector configurations.

Figure 4:
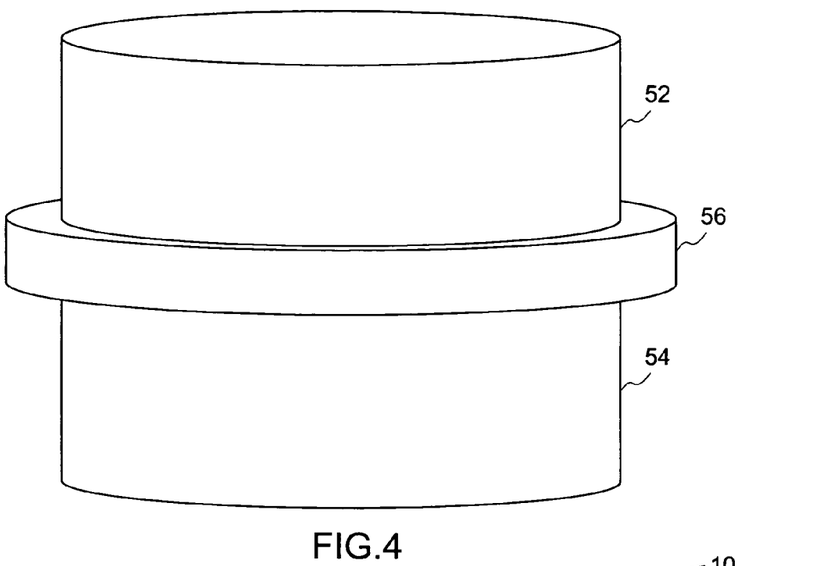
FIG. 4 is a diagrammatical representation of an exemplary source-detector configuration for use with the system of FIG. 1.
Figure 5:
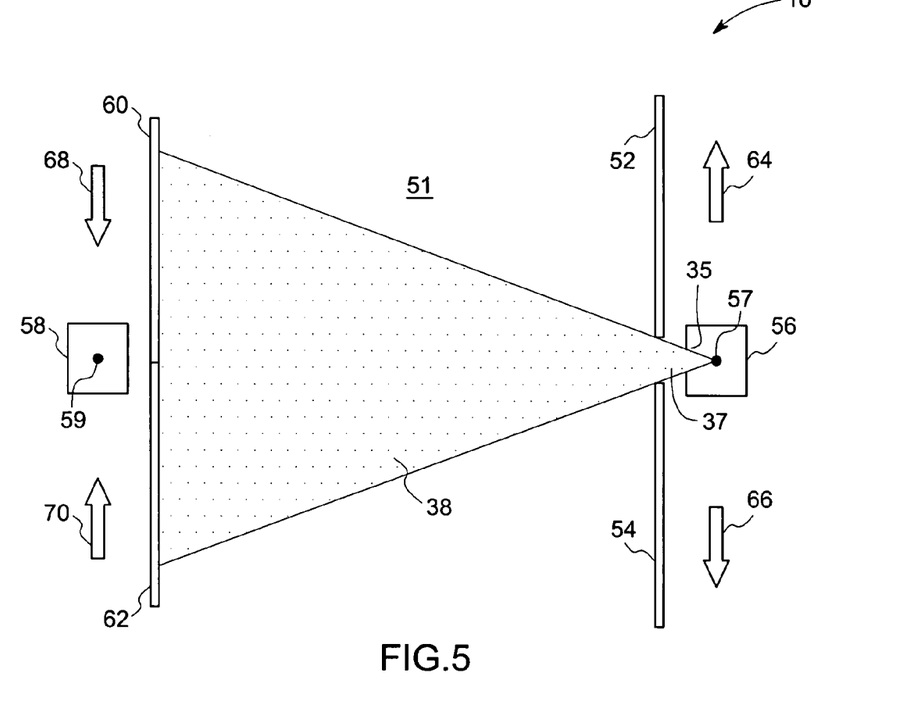
FIG. 5 is a diagrammatical representation of an imaging technique employing the detector movement to capture more complete projection data and for use with the configuration of FIG. 4.

FIG. 4 illustrates a source-detector configuration which may be used in a helical scanning mode where a distributed radiation source 56 is flanked by two detectors 52 and 54. FIG. 5 illustrates an exemplary embodiment for use by the imaging system 10 for scanning a portion of volume to be imaged (or a desired portion of an imaging volume), depicted generally by reference numeral 51, for the source-detector configuration of FIG. 4. The source 56 in FIG. 5 is triggered to emanate a radiation beam 38 to be captured by the detectors 60 and 62, located generally opposite to the source 56. As the source 56 is about to be triggered, in one example, at least one of the detectors 52 and 54, positioned generally adjacent to the source 56, are configured to move generally transversely in a direction generally shown by arrows 64 and 66 respectively to allow the radiation beam 38 to emanate in an unimpeded manner, by opening an aperture 35 for at least one individual source position 57 within the distributed radiation source 56 to emanate the radiation beam 38 through the unimpeded path, shown generally by the reference numeral 37. At the same time, in a specific example, at least one of the detectors 60 and 62 moves generally transversely in the direction shown by arrows 68 and 70 respectively, to cover the aperture required for source position 59 in the source 58 (which may be the same vacuum enclosure indicated by source 56), located generally opposite to the source 56, in order to intercept the transmitted radiation beam 38. In helical scanning mode, as would be appreciated by those skilled in the art, when the source 58 is triggered (not shown), the detectors 60 and 62 move in a direction opposite to the directional arrows 68 and 70 respectively to open up an aperture for source position 59. At the same time the detectors 52 and 54 move in a direction opposite to the directional arrows 64 and 66 respectively to fully intercept the transmitted X-ray radiation and close the aperture 35 required for source position 57. As a result of this configuration, projection data within a gap region typically provided between the two area detectors in a specifically stationary configuration is effectively captured, since the gap region is eliminated. Additionally, the angular extent of the detectors can be chosen to reduce the number and timing of detector movements during a scan.

It will be well understood by those skilled in the art that several combinations and sub-combinations of the configuration described hereinabove are possible to suit a particular scanning protocol or imaging application. For example, in one embodiment, a first detector (52 or 54) is positioned generally adjacent to the distributed radiation source 56 and is configured to move transversely to allow the radiation beam 38 to illuminate the desired portion of the imaging volume through the unimpeded path 37 by opening an aperture 35 for at least one individual position 57 for the distributed radiation source 56. A second detector (60 or 62) is positioned generally opposite to the first detector (52 or 54), and configured to move transversely, to intercept the transmitted radiation beam 38 by covering at least a portion of the aperture required by another individual source position 59, of the distributed radiation source 58, located generally opposite to the distributed radiation source 56. In another example, a first set of at least two detectors (52 and 54) are positioned generally adjacent to the distributed radiation source 56, and configured to move transversely to allow the radiation beam 38 through the unimpeded path 37, by opening an aperture 35 for at least one individual source position 57 for the distributed radiation source 56 to emanate the radiation beam 38. A second set of at least two detectors (60 and 62) are positioned generally opposite to the at first set of at least two detectors (52 and 54), and configured to move transversely to intercept the transmitted radiation beam 38, by covering at least a portion of an aperture required for another individual source position 59 of the distributed radiation source 58, located generally opposite to the distributed radiation source 56.

In one exemplary embodiment, the detectors 52 and 60 (or alternatively 54 and 62) form a single closed structure (such as a full ring comprised with planar sections or cylindrical sections) and nutate, to cover at least a portion of the aperture 35 required for source positions 57 and 59, located generally opposite to the distributed radiation sources 56 and 58 in order to intercept the transmitted radiation beam 38, and collect projection data which is usually missing in a helical scanning mode with a fully stationary configuration of the distributed X-ray source and detector. Nutating is defined as the motion that occurs when the symmetry axis of the ring is slightly tilted with respect to and rotating around the longitudinal axis of the scanner.

Figure 6:
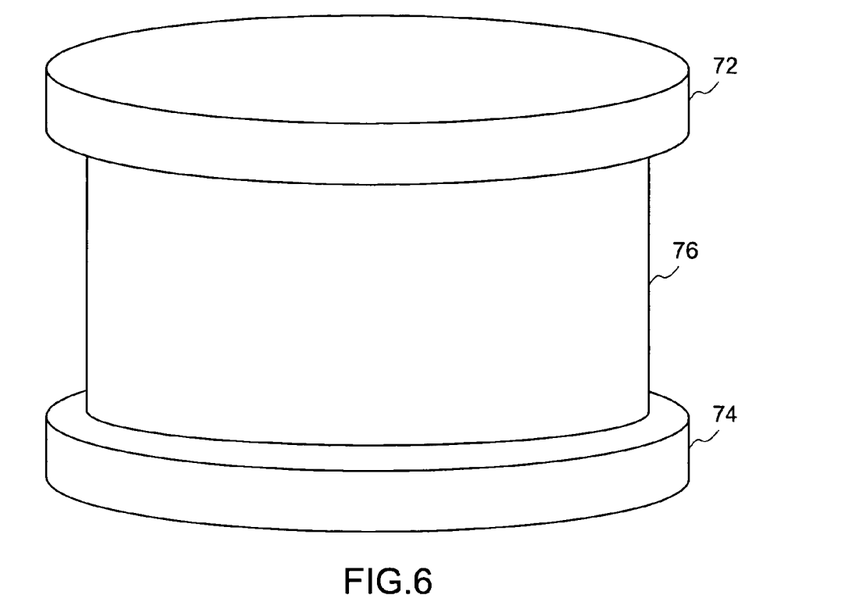
FIG. 6 is a diagrammatical representation of another exemplary source-detector configuration for use with the system of FIG. 1.
Figure 7:
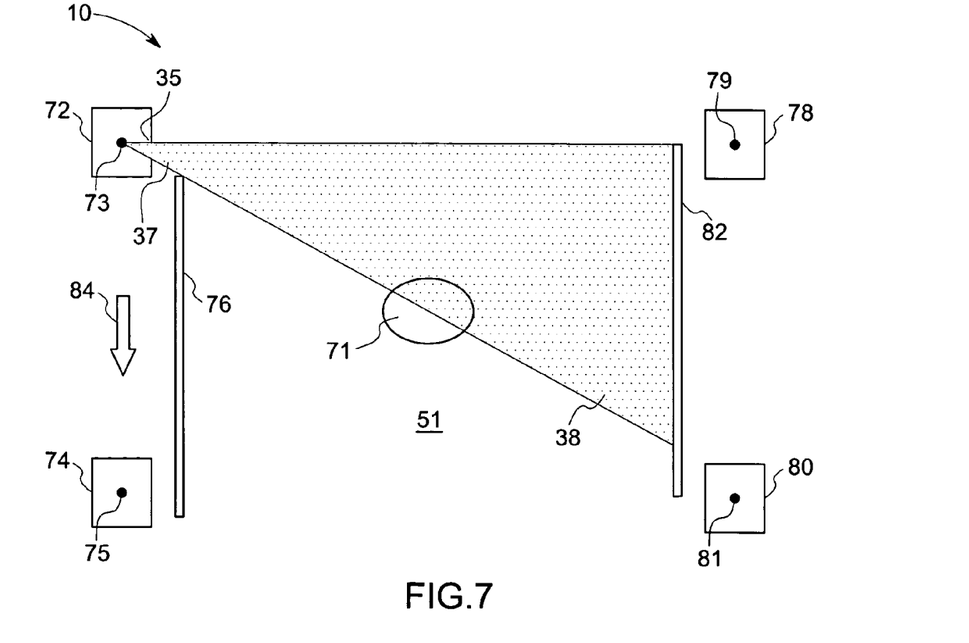
FIG. 7 is a diagrammatical representation of an imaging technique employing detector movement to capture more complete projection data and for use with the configuration of FIG. 6.

FIG. 6 illustrates another exemplary source-detector configuration which may be used in an axial scanning mode where a detector 76 is positioned between two distributed radiation sources 72 and 74. FIG. 7 is an exemplary embodiment for use by the imaging system 10 for scanning a desired portion of an imaging volume depicted generally by 51, for the source-detector configuration of FIG. 6. Again as it would be appreciated by those skilled in the art, typically in axial scanning mode, as the sources 72, 74, 78, and 80 are triggered, the projection data from a region generally at the center of the field of view, depicted generally by reference numeral 71 is not captured due to the fully stationary source-detector geometry and the finite separation between the source and the edge of the detector. To overcome this, in an exemplary embodiment as shown in FIG. 7, the source 72 is triggered to emanate the radiation beam 38 as the detector 76 (first detector) moves in the direction 84 from a central position to open an aperture 35 required by the source position 73, allowing an unimpeded path 37 for the radiation beam 38. In a specific example the detector 76 moves generally transversely to open the aperture 35 for source position 73. On the opposite side of the source-detector configuration (generally opposite to the source 72), the detector 82 (second detector) is configured to be at the central position to cover both the aperture required by source position 79 of the source 78 and aperture required by source position 81 of the source 80, thereby measuring the requisite projection data need for image reconstruction. In one exemplary embodiment, the detector 82 is a single structure and nutates, to cover at least a portion of the aperture required for source positions 79 and 81, located generally opposite to the distributed radiation sources 72 and 74 in order to intercept the transmitted radiation beam 38, and collect information pertaining to region 71, which is usually missing in axial scanning mode with a fully stationary configuration of the distributed X-ray source and detector. Detector movement operations required when source positions 81, 73, and 75 are activated within source 80, 72, and 74, respectively are easily inferred from the above discussion. Moreover, one or more of sources 78, 80, 72, and 74 may comprise the same vacuum enclosure.

It would be appreciated by those skilled in the art that the nutating motion also results in simultaneous covering of the aperture 35 required by source position 73 and 75 and uncovering the aperture required by source position 79 and also appropriate positioning of the detector elements to effectively capture the transmitted radiation beam from activated source positions. Other nutating motions are easily inferred to enable measurement of projection data within region 71 from all source positions, as shown on FIG. 7.

As discussed with respect to the helical scanning mode, various combinations and sub-combinations of the above configuration described hereinabove are possible to suit a particular scanning protocol or imaging application.

Figure 8:
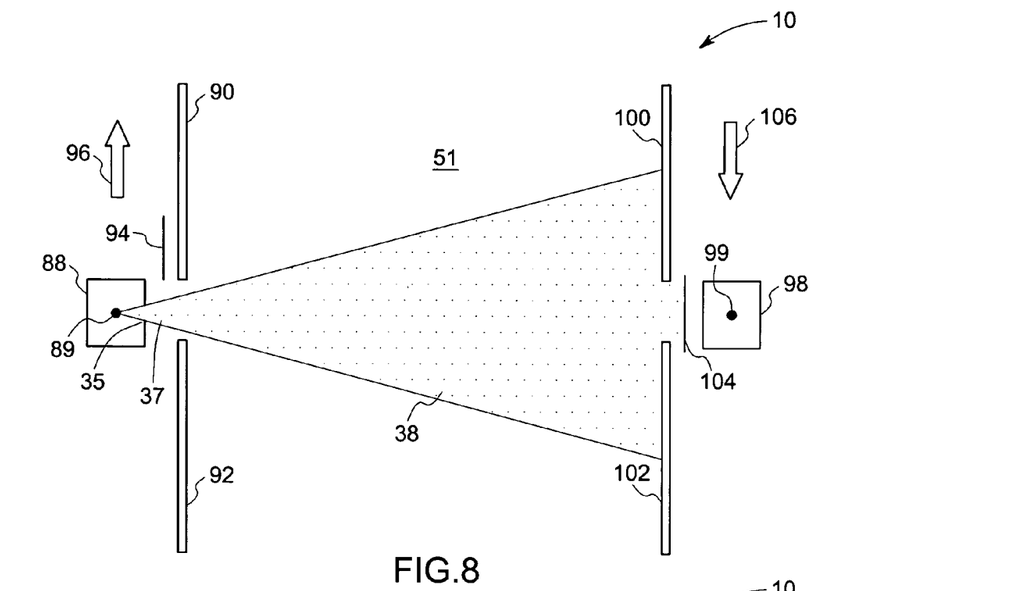
FIG. 8 is a diagrammatical representation of another imaging technique employing movement of detector sections to capture more complete projection data and for use with the configuration of FIG. 4.
Figure 9:
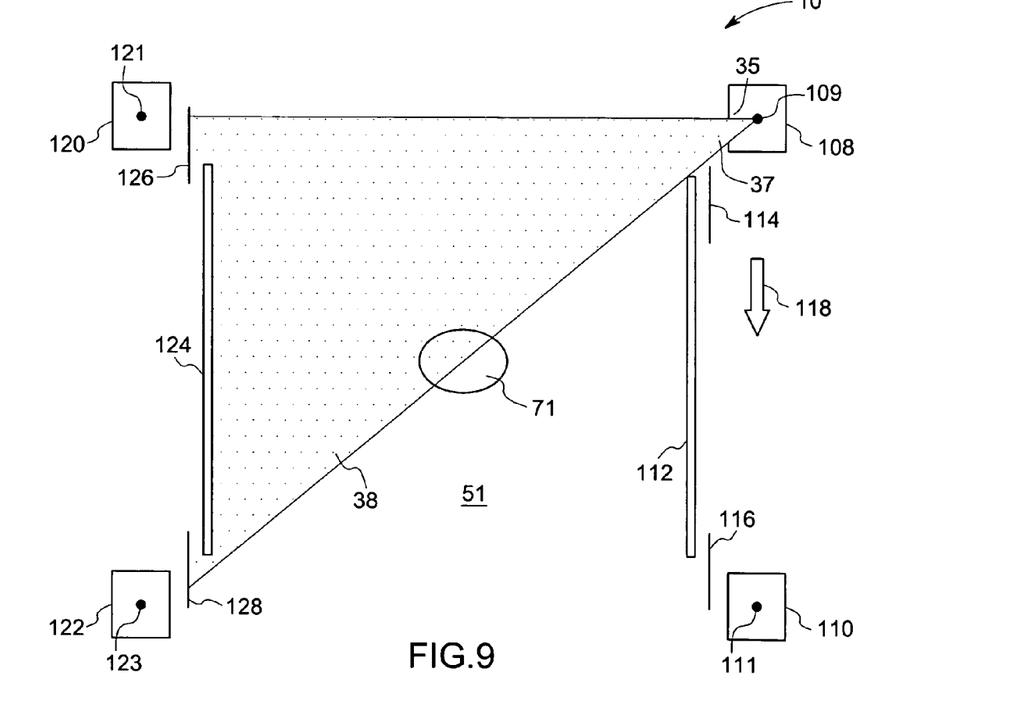
FIG. 9 is a diagrammatical representation of an alternative imaging technique employing movement of detector sections to capture more complete projection data and for use with the configuration of FIG. 6.

FIG. 8 and FIG. 9 illustrate exemplary embodiments of typical helical and axial scanning configurations, respectively, where a section of the detector, for example detector sections 94, 104, 114, 116, 126 and 128 are moved in order to provide an aperture or intercept the X-ray radiation (radiation beam).

FIG. 8 shows an imaging system 10 typically used in the helical scanning configuration for imaging a desired portion of an imaging volume depicted generally by 51, similar to the scanning configuration as described in FIG. 4 and FIG. 5. The detector section 94 is moved generally transversely in the direction 96 to open at least one individual aperture 35 for source position 89 of the source 88 to allow an unimpeded path 37 for the radiation beam 38 to emanate, and the detector section 104 is moved to intercept the transmitted radiation beam 38, by covering the aperture for source position 99 of the distributed radiation source 98, located generally opposite to source 88. Once again, as discussed in reference to FIG. 5, and as with all configurations shown in FIG. 4–FIG. 10, the angular extent of the detector sections is preferably chosen to minimize the number of times that the sections have to be repositioned during a scan.

FIG. 9 shows an imaging system 10 typically used in the axial scanning configuration for imaging a volume 51, similar to the scanning configuration as described in relation with FIG. 6 and FIG.7. The section 114 (a first section) is moved in the direction generally shown by 118, to open an aperture 35 for source position 109 for the source 108 to allow an unimpeded path 37 for the radiation beam 38, thereby capturing the projection data measurements from the region 71. Alternately, in a specific example, a combination of the detectors are configured to nutate to cover at least partially the aperture required by an inactivated source position, thereby enabling projection data measurements including region 71 on FIG. 9, and open the aperture required by the activated source position, thereby enabling the radiation beam to fully illuminate the requisite portion of the imaging volume. As it would be appreciated by those skilled in the art, as in the helical scanning configurations, the angular coverage of the detector panels and sections as described for axial scanning configuration are chosen to minimize movement during an axial scanning interval.

Figure 10:
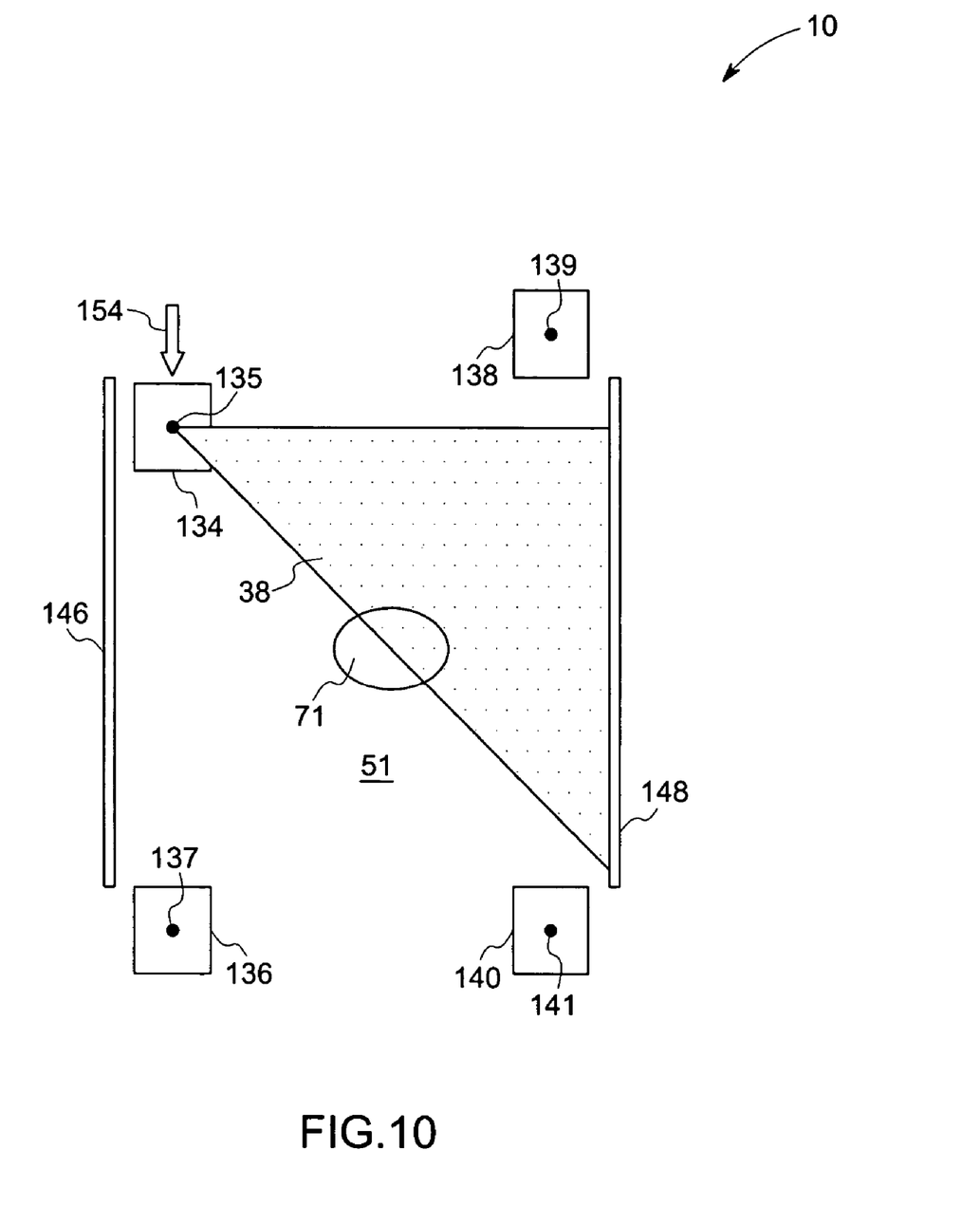
FIG. 10 is a diagrammatical representation of an alternative imaging technique employing movement of a source to capture more complete projection data.

Besides the configurations described hereinabove where the detector or the detector section is displaceable, in certain specific configurations the one or more distributed radiation sources are configured to be displaceable to illuminate the desired portion of the imaging volume for measurement of more mathematically complete projection data and for the detector to receive the radiation beam. FIG. 10 illustrates a specific embodiment wherein the imaging system 10 includes a source (134, 136, 138, 140) configured to be displaced or moved to illuminate the imaging volume 51 for measurement of more mathematically complete projection data with the radiation beam 38. The embodiment is described with respect to the axial scanning mode, but the technique as would be appreciated by those skilled in the art can be applied to other scanning configurations as well, for example in the helical scanning mode. FIG. 10 illustrates an exemplary configuration for the moving radiation source 134, to more completely illuminate the imaging volume 51. In this configuration the sources and detectors are positioned such that only the source 134 which is triggered to emanate the radiation beam 38 moves in the direction 154 to more completely illuminate the imaging volume 51 and the transmitted radiation beam is intercepted effectively by the detector 148. The above described source movement also results in effectively capturing the missing information from region 71. Again as would be appreciated by those skilled in the art, various combinations and sub-combinations of the source movements are possible for both axial and scanning modes, based on the above technique. Also combinations and sub-combinations where both the source and detector are displaced are possible according to aspects of the present technique.

As it would be appreciated by those skilled in the art, the configurations described hereinabove overcome the limitations of mathematically incomplete projection data measurement, both in the axial and helical scanning configurations of stationary CT system configurations. Specifically, in axial scanning mode, the limitation of incomplete projection data, at the center of the field of view, is eliminated, and in helical scanning mode the limitation of incomplete projection data for an angular range of an effective source rotation, is eliminated. This results in more mathematically complete projection data measurement for improved image quality in cone-beam reconstructions for stationary CT applications.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An imaging system comprising:
one or more distributed X-ray sources substantially surrounding a desired portion of an imaging volume and configured to emanate a radiation beam from a plurality of individual source positions around the imaging volume; and
one or more X-ray detectors configured to receive the radiation beam transmitted through the desired portion of the volume,
wherein at least one of the one or more distributed X-ray sources or the one or more X-ray detectors are displaceable transversely and one or more X-ray detectors are stationary to allow an unimpeded path for the radiation beam to illuminate the desired portion of the imaging volume and for the X-ray detector to receive the radiation beam.

2. The system of claim 1, wherein the one or more X-ray detectors are configured to move transversely to allow the radiation beam to illuminate the desired portion of the imaging volume by opening at least one individual aperture for the one or more distributed X-ray sources to emanate the radiation beam.

3. The system of claim 1, wherein one or more sections of the one or more X-ray detectors are configured to move transversely and one or more sections of the one or more X-ray detectors are configured to be stationary to allow the radiation beam to illuminate the desired portion of the imaging volume by opening at least one individual aperture for the one or more distributed X-ray sources to emanate the radiation beam.

4. The system of claim 1, wherein the one or more X-ray detectors are configured to nutate to allow the radiation beam to illuminate the desired portion of the imaging volume by opening at least one individual aperture for the one or more distributed radiation sources to emanate the radiation beam.

5. The system of claim 1, wherein one or more sections of the one or more X-ray detectors are configured to nutate and one or more sections of the one or more X-ray detectors are configured to be stationary to allow the radiation beam to illuminate the desired portion of the imaging volume by opening at least one individual aperture for the one or more distributed X-ray sources to emanate the radiation beam.

6. The system of claim 1, wherein the one or more X-ray detectors are configured to move transversely to intercept the radiation beam by covering at least a portion of the aperture from one or more individual X-ray source positions located generally opposite to the one or more distributed X-ray sources emanating the radiation beam.

7. The system of claim 1, wherein the one or more X-ray detectors are configured to nutate to intercept the radiation beam by covering at least a portion of the aperture of one or more individual X-ray source positions located generally opposite to the one or more distributed X-ray sources emanating the radiation beam.

8. The system of claim 1, wherein one or more sections of the one or more X-ray detectors are configured to move transversely and one or more sections of the one or more X-ray detectors are configured to be stationary to intercept the radiation beam by covering at least a portion of the aperture of one or more individual X-ray source positions located generally opposite to the one or more distributed X-ray sources emanating the radiation beam.

9. The system of claim 1, wherein at least one section of the one or more X-ray detectors are configured to nutate to intercept the radiation beam by covering at least partially the aperture of at least one different individual X-ray source position located generally opposite to the one or more distributed X-ray sources emanating the radiation beam.

10. An imaging system comprising:
one or more distributed X-ray sources substantially surrounding a desired portion of an imaging volume and configured to emanate a radiation beam from a plurality of individual X-ray source positions around the imaging volume; and
one or more X-ray detectors configured to be stationary and one or more X-ray detectors configured to move transversely for at least one of:
causing the radiation beam to illuminate the desired portion of the imaging volume by opening at least one individual aperture for the one or more X-ray sources to emanate the radiation beam; and
intercepting the radiation beam by covering at least a portion of the aperture required by one or more individual X-ray positions located generally opposite to the one or more distributed X-ray sources emanating the radiation beam.

11. An imaging system comprising:
one or more distributed X-ray sources substantially surrounding a desired portion of an imaging volume and configured to emanate a radiation beam from a plurality of individual X-ray source positions around the imaging volume; and
one or more sections of one or more X-ray detectors configured to be stationary and one or more sections of one or more X-ray detectors configured to move transversely for at least one of:
causing the radiation beam to illuminate the desired portion of the imaging volume by opening at least one individual aperture for the one or more distributed X-ray sources to emanate the radiation beam; and
intercepting the radiation beam by covering at least a portion of the aperture required by one or more individual X-ray source positions located generally opposite to the one or more distributed X-ray sources emanating the radiation beam.

12. An imaging system comprising:
one or more distributed X-ray sources substantially surrounding a desired portion of an imaging volume and configured to emanate a radiation beam from a plurality of individual X-ray source positions around the imaging volume; and
one or more X-ray detectors configured to be stationary and one or more X-ray detectors configured to at least one of nutate or move transversely for at least one of:
causing the radiation beam to illuminate the desired portion of the imaging volume by opening at least one individual aperture for the one or more distributed X-ray sources to emanate the radiation beam; and
intercepting the radiation beam by covering at least a portion of the aperture of at least one different individual X-ray source position located generally opposite to the one or more distributed X-ray sources emanating the radiation beam.

13. An imaging system comprising:
one or more distributed X-ray sources substantially surrounding a desired portion of an imaging volume and configured to emanate a radiation beam from a plurality of individual X-ray source positions around the imaging volume; and
one or more sections of one or more X-ray detectors configured to be stationary and one or more sections of one or more X-ray detectors configured to at least one of nutate or move transversely for at least one of:
causing the radiation beam to illuminate the desired portion of the imaging volume by opening at least one individual aperture for the one or more distributed X-ray sources to emanate the radiation beam; and
intercepting the radiation beam by covering at least a portion of the aperture of at least one different individual X-ray source position located generally opposite to the one or more distributed X-ray sources emanating the radiation beam.

14. A stationary CT system comprising:
a plurality of X-ray sources arranged relative to a volume to be imaged, each X-ray source configured to emanate an X-ray beam; and
a plurality of X-ray detectors arranged generally across from respective X-ray sources, wherein at least one of an X-ray source from the plurality of X-ray sources or a X-ray detector from the plurality of X-ray detectors are configured to be displaced transversely to allow an unimpeded path for the X-ray beam to illuminate a desired portion of an imaging volume and for the X-ray detector to receive a transmitted X-ray beam, and wherein the remaining X-ray detectors from the plurality of X-ray detectors are stationary.

15. The system of claim 14, wherein the X-ray detector is configured to at least one of nutate or move transversely and to open an aperture for an adjacent X-ray source to emanate the X-ray beam.

16. The system of claim 14, wherein a section of the X-ray detector is configured to at least one of nutate or move transversely and one or more sections of the plurality of X-ray detectors are configured to be stationary to open an aperture for an adjacent X-ray source to emanate the X-ray beam.

17. The system of claim 14, wherein the X-ray detector is configured to at least one of nutate or move transversely to cover at least a portion of an aperture for one or more adjacent X-ray sources located generally opposite to an X-ray source emanating the X-ray beam.

18. The system of claim 14, wherein a section of the X-ray detector is configured to at least one of nutate or move transversely and one or more sections of the plurality of X-ray detectors are configured to be stationary to cover at least a portion of an aperture for one or more adjacent X-ray sources located generally opposite to an X-ray source emanating the X-ray beam.

19. An imaging system for scanning a volume to be imaged, the system comprising:
one or more distributed X-ray sources substantially surrounding a desired portion of an imaging volume and configured to emanate a radiation beam from a plurality of individual X-ray source positions around the imaging volume;
a control circuit operably coupled to the source;
one or more X-ray detectors to receive a transmitted radiation;
a motor controller configured to displace at least one of the source and the detector;
a processing circuit operably coupled to the detector configured to receive a plurality of projection images and to form one or more reconstructed slices representative of the volume being imaged; and
an operator workstation operably coupled to the processing circuit configured to display the one or more reconstructed slices,
wherein at least one of the one or more distributed X-ray sources or the one or more X-ray detectors are displaceable transversely and one or more X-ray detectors are stationary to allow an unimpeded path for generation of the radiation beam and the reception of the transmitted radiation beam.

20. The system of claim 19 further comprising:
one or more X-ray detectors configured to be are stationary; and
one or more X-ray detectors configured to at least one of nutate or move transversely for at least one of:
allowing the radiation beam to illuminate the desired portion of the imaging volume by opening at least one individual aperture for the one or more distributed X-ray sources to emanate the radiation beam; and
intercepting the radiation beam by covering at least a portion of the aperture of at least one different individual X-ray source positions located generally opposite to the one or more distributed X-ray sources emanating the radiation beam.

21. The system of claim 19 further comprising:
one or more sections of one or more X-ray detectors configured to be stationary; and
one or more sections of one or more X-ray detectors configured to one of nutate or move transversely for at least one of:
allowing the radiation beam to illuminate the desired portion of the imaging volume by opening at least one individual aperture for the one or more distributed X-ray sources to emanate the radiation beam; and
intercepting the radiation beam by covering at least a portion of the aperture of at least one different individual X-ray source positions located generally opposite to the one or more distributed X-ray sources emanating the radiation beam.

22. An imaging system comprising:
one or more distributed X-ray sources substantially surrounding a desired portion of an imaging volume and configured to emanate a radiation beam from a plurality of individual X-ray source positions around the imaging volume; and
one or more sections of one or more X-ray detectors configured to be stationary; and
one or more sections of one or more X-ray detectors configured to one of nutate or move transversely for at least one of:
allowing the radiation beam to illuminate the desired portion of the imaging volume by opening at least one individual aperture for the one or more distributed X-ray sources to emanate the radiation beam; and
intercepting the radiation beam by covering at least a portion of the aperture of at least one different individual X-ray source positions located generally opposite to the one or more distributed X-ray sources emanating the radiation beam.

23. An imaging system comprising:
one or more distributed X-ray sources substantially surrounding a desired portion of an imaging volume and configured to emanate a radiation beam from a plurality of individual X-ray source positions around the imaging volume; and
one or more X-ray detectors configured to receive a transmitted radiation beam,
wherein at least one of the X-ray source or the X-ray detector is displaceable transversely and the one or more X-ray detectors are stationary to allow illumination of the desired portion of the imaging volume and for the X-ray detector to receive the transmitted radiation beam.

24. An imaging system comprising:
one or more distributed X-ray sources substantially surrounding a desired portion of an imaging volume and configured to emanate a radiation beam from a plurality of individual X-ray source positions around the imaging volume; and one or more X-ray detectors configured to receive a transmitted radiation beam, wherein at least one of the X-ray source or the X-ray detector is nutated or displaced transversely and the one or more X-ray detectors are stationary to allow illumination of the desired portion of the imaging volume and for the X-ray detector to receive the transmitted radiation beam.

25. A method of scanning a volume to be imaged, the method comprising:

triggering a distributed X-ray source for emanating a radiation beam;

displacing transversely one or more X-ray detectors positioned generally adjacent to the distributed X-ray source to allow an unimpeded path for the radiation beam to illuminate an imaging volume; and displacing one or more X-ray detectors positioned generally opposite to the distributed X-ray source to intercept a transmitted radiation beam, wherein the one or more X-ray detectors comprise stationary detectors and movable detectors.

26. The method of claim 25 further comprising displacing a section of one or more X-ray detectors for allowing an unimpeded path for the radiation beam to illuminate the imaging volume, wherein the one or more X-ray detectors comprise stationary sections and movable sections.

27. The method of claim 25 further comprising displacing a section of one or more X-ray detectors for intercepting the transmitted radiation beam, wherein the one or more X-ray detectors comprise stationary sections and movable sections.

* * * * *

UNITED STATES PATENT AND TRADEMARK OFFICE
CERTIFICATE OF CORRECTION

| | | |
|---|---|---|
| PATENT NO. | : 7,142,629 B2 | Page 1 of 1 |
| APPLICATION NO. | : 10/814537 | |
| DATED | : November 28, 2006 | |
| INVENTOR(S) | : Peter Michael Edic and Bruno Kristiaan Bernard De Man | |

It is certified that error appears in the above-identified patent and that said Letters Patent is hereby corrected as shown below:

Title Page, Item (75) Inventors:
    The spelling of the inventor "Peter Michael Edie" is incorrect. The correct spelling should be "Peter Michael Edic".

Signed and Sealed this

Eighteenth Day of August, 2009

David J. Kappos
*Director of the United States Patent and Trademark Office*